United States Patent
Kääriäinen et al.

(10) Patent No.: US 10,139,392 B2
(45) Date of Patent: Nov. 27, 2018

(54) METHOD AND APPARATUS FOR BREATH ANALYSIS

(71) Applicant: Teknologian tutkimuskeskus VTT Oy, Espoo (FI)

(72) Inventors: Teemu Kääriäinen, Espoo (FI); Albert Manninen, Espoo (FI)

(73) Assignee: TEKNOLOGIAN TUTKIMUSKESKUS VTT OY, Espoo (FI)

( * ) Notice: Subject to any disclaimer, the term of this patent is extended or adjusted under 35 U.S.C. 154(b) by 0 days.

(21) Appl. No.: 15/825,187

(22) Filed: Nov. 29, 2017

(65) Prior Publication Data
US 2018/0224424 A1    Aug. 9, 2018

(30) Foreign Application Priority Data
Feb. 6, 2017 (FI) ...................... 20175098

(51) Int. Cl.
| A61B 5/08 | (2006.01) |
|---|---|
| G01N 33/497 | (2006.01) |
| G01N 21/62 | (2006.01) |
| A61B 5/097 | (2006.01) |

(52) U.S. Cl.
CPC .......... G01N 33/497 (2013.01); A61B 5/082 (2013.01); G01N 21/62 (2013.01); A61B 5/097 (2013.01); G01N 2033/4975 (2013.01)

(58) Field of Classification Search
CPC ........ A61B 5/0813; A61B 5/082; A61B 5/097
See application file for complete search history.

(56) References Cited

U.S. PATENT DOCUMENTS

| 4,090,078 A | 5/1978 | Heim |
|---|---|---|
| 6,180,414 B1 | 1/2001 | Katzman |
| 2003/0109795 A1 | 6/2003 | Webber |
| 2003/0216660 A1* | 11/2003 | Ben-Oren .............. A61B 5/083 |
| | | 600/532 |
| 2011/0295140 A1 | 12/2011 | Zaidi et al. |
| 2012/0234076 A1* | 9/2012 | Rigas .................. G01N 33/497 |
| | | 73/23.3 |
| 2014/0114206 A1 | 4/2014 | Joseph |
| 2014/0194703 A1 | 7/2014 | Wondka et al. |

(Continued)

FOREIGN PATENT DOCUMENTS

| EP | 3009838 A1 | 4/2016 |
|---|---|---|
| WO | WO-2016200948 A1 | 12/2016 |

OTHER PUBLICATIONS

Finnish Search Report issued by the Finnish Patent and Trademark Office in relation to Finnish Patent Application No. 20175098 dated May 5, 2017 (2 pages).

(Continued)

*Primary Examiner* — Christian Jang
(74) *Attorney, Agent, or Firm* — Robert P. Michal, Esq.; Carter, DeLuca, Farrell & Schmidt, LLP

(57) ABSTRACT

A method and an apparatus for breath analysis, the method comprising determining an isotopic composition profile, or a concentration profile of a species, of a first breath cycle; determining a threshold; determining a sampling time; and measuring the isotopic composition, or concentration of the species, during a second breath cycle at the sampling time triggered by reaching the threshold.

13 Claims, 3 Drawing Sheets

(56) References Cited

U.S. PATENT DOCUMENTS

2015/0301019 A1 10/2015 Smith
2016/0377534 A1 12/2016 Maekawa et al.

OTHER PUBLICATIONS

Communication of Acceptance issued by the Finnish Patent and Registration Office in relation to Finnish Patent Application No. 20175098 dated Sep. 18, 2017 (5 pages).
International Search Report issued by the Finnish Patent and Registration Office acting as the International Searching Authority in relation to International Patent Application No. PCT/FI2018/050073 dated Apr. 13, 2018 (6 pages).

* cited by examiner

METHOD AND APPARATUS FOR BREATH ANALYSIS

CROSS-REFERENCE TO RELATED APPLICATIONS

This Application claims priority to Finnish Application No. 20175098, filed Feb. 6, 2017 the entire disclosure of which is incorporated herein by reference.

TECHNICAL FIELD

The present application generally relates to determining the composition of gas. In particular, but not exclusively, the present application relates to determining the isotopic composition of a gas. In particular, but not exclusively, the present application relates determining the isotopic composition of breath or a concentration of a measured species in breath.

BACKGROUND

This section illustrates useful background information without admission of any technique described herein being representative of the state of the art.

Breath diagnostics is a fast growing trend in the medical field. Especially isotope-selective breath analysis has been applied for diagnostics and monitoring of numerous diseases and conditions, including diabetes, liver function, gastric infections and sepsis. The selectivity and sensitivity of the methods rely on precise knowledge of the isotopic composition of the exhaled gas and accordingly the determination of isotopic composition is of great interest.

Most of the currently used technologies for determining isotopic composition are based on sampling bags, wherein only a part of the breath cycle is captured, leading to decreased reliability of determination, especially as it was recently shown by the inventors that the isotopic composition changes during the exhalation cycle and, therefore, affects the determination of isotopic composition. The results on the isotope composition changing during a breath cycle have been shown in a conference paper titled "Compact, Real-Time Analyzer for C-13 and O-18 Isotope Ratios of Carbon Dioxide in Breath Air" by T. Kaariainen et. al. at the Conference on Lasers and Electro-Optics, CLEO 2016 in San Jose, Calif., United States on 5-10 Jun. 2016.

Real-time breath analysis according to the current invention, for example using an optical detector with a low volume multipass cell for example as described in an unpublished patent application of the inventors FI20155833, makes it possible to sample a correct portion of the exhaled breath and thus to tackle possible errors arising from the sampling. It is the aim of the current invention to provide a method and apparatus that mitigates for example the above problems of the state of the art and/or provides a reliable determination of composition of a gas, in particular isotopic composition of breath, or a concentration of a measured species, such as $CO_2$, in breath.

SUMMARY

Various aspects of examples of the invention are set out in the claims.

According to a first example aspect of the present invention, there is provided a method for breath analysis, comprising determining an isotopic composition profile, or a concentration profile of a species, of a first breath cycle;
determining a threshold;
determining a sampling time; and
measuring the isotopic composition, or concentration of the species during a second breath cycle at the sampling time triggered by reaching the threshold.

The method may further comprise showing as a result the measured isotopic composition or concentration.

Determining an isotopic composition profile of a first breath cycle may comprise measuring the absorption of various isotopologues of carbon dioxide.

Determining a threshold may comprise determining a predetermined absorption of a selected isotopologue.

Determining a sampling time may comprise determining a time or a time frame on or during which the measurement is carried out during the second breath cycle.

According to a second example aspect of the present invention, there is provided an apparatus for breath analysis, comprising a measurement unit configured to measure an absorption of various isotopologues of carbon dioxide during a breath cycle;
a sampling unit configured to enable the exhaled breath to be conducted to the measurement unit; and
a control unit; wherein
the control unit is configured to cause the apparatus to determine an isotopic composition, or a concentration profile of a species, of a first breath cycle, to determine a threshold and a sampling time based thereon, and to measure the isotopic composition, or concentration of the species, during a second breath cycle at the sampling time triggered by reaching the threshold.

The measurement unit may comprise a multipass cell, an optical unit comprising an optical source and a detector and a gas handling unit.

The sampling unit may comprise an inlet into which the breath to be measured is conducted to.

The control unit may comprise a processor configured to control the apparatus.

The control unit may comprises a user interface unit configured to show the result of the determination of isotopic composition or concentration.

The apparatus may be configured to show whether the result of the determination of the isotopic composition of breath, or concentration of the species, is indicative of a disease or a condition.

According to a third example aspect of the present invention, there is provided a computer program comprising computer code for causing performing the method of the first example aspect of the present invention, when executed by an apparatus.

According to a fourth example aspect of the present invention, there is provided a non-transitory memory medium comprising the computer program of the third example aspect of the present invention.

Different non-binding example aspects and embodiments of the present invention have been illustrated in the foregoing. The embodiments in the foregoing are used merely to explain selected aspects or steps that may be utilized in implementations of the present invention. Some embodiments may be presented only with reference to certain example aspects of the invention. It should be appreciated that corresponding embodiments may apply to other example aspects as well.

BRIEF DESCRIPTION OF THE DRAWINGS

For a more complete understanding of example embodiments of the present invention, reference is now made to the following descriptions taken in connection with the accompanying drawings in which.

DETAILED DESCRIPTION OF THE DRAWINGS

The present invention and its potential advantages are understood by referring to FIGS. 1 through 5 of the drawings. In this document, like reference signs denote like parts or steps.

Figure 1:
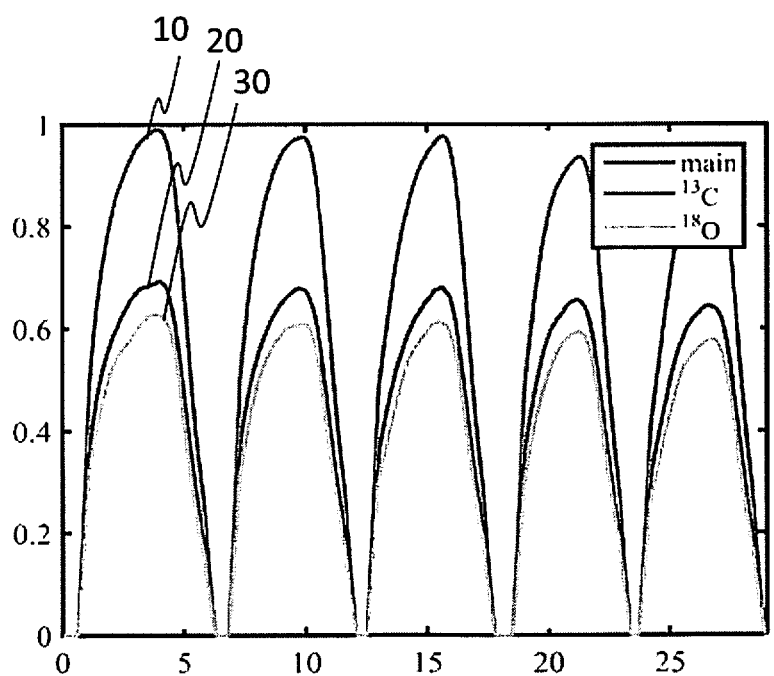
FIG. 1 shows an example of breath cycles measured with an apparatus according to an embodiment of the invention.

FIG. 1 shows an example of breath cycles measured with an apparatus according to an embodiment of the invention. The graph shows a measured absorption of light in the analyzer at the vertical axis and time in seconds at the horizontal axis. The measured absorption is shown at a relative scale in which the highest absorption has the value of 1. The measured absorption is shown for different isotopologues of $CO_2$ of the exhaled air, i.e. for $^{16}O^{12}C^{16}O$, $^{16}O^{13}C^{16}O$ and $^{16}O^{12}C^{18}O$, or hereinafter referred to as main, 13C and 18O isotopes or isotopologues. The measured absorption of the main isotope is shown at 10, the measured absorption of the 13C isotope is shown at 20 and the measured absorption of the 18O isotope is shown at 30.

Figure 2:
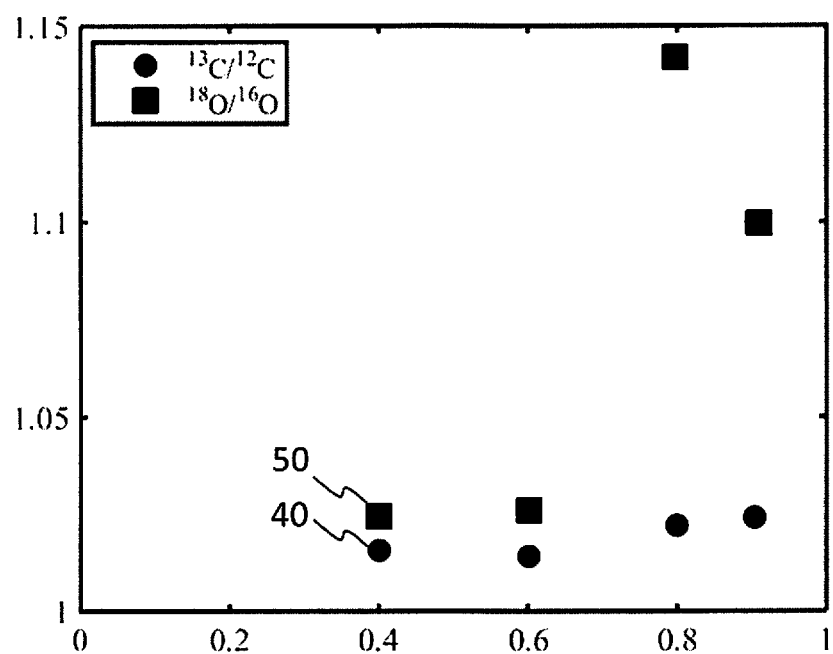
FIG. 2 shows example isotope ratios at different portions of a single example breath cycle measured with an apparatus according to an embodiment of the invention.

FIG. 2 shows example isotope ratios at different portions of breath cycle measured with an apparatus according to an embodiment of the invention. FIG. 2 shows at the vertical axis the ratio of 13C and 12C isotopologues 40 and the ratio of 18O and 16O isotopologues 50 with respect to the portion of the breath cycle expressed as the measured absorption at the horizontal axis. As can be seen from FIG. 2, the ratios of the isotopologues change during the breath cycle significantly and accordingly the determination of isotopologue content of breath is dependent on the sampling and/or sampling time of the ratios during the cycle. The ratios of the isotopologues change during the cycle for example because the exhaled air originates from different portions of the respiratory system, i.e. from mouth, throat, main lung volume and deep parts of the lungs.

Figure 3:
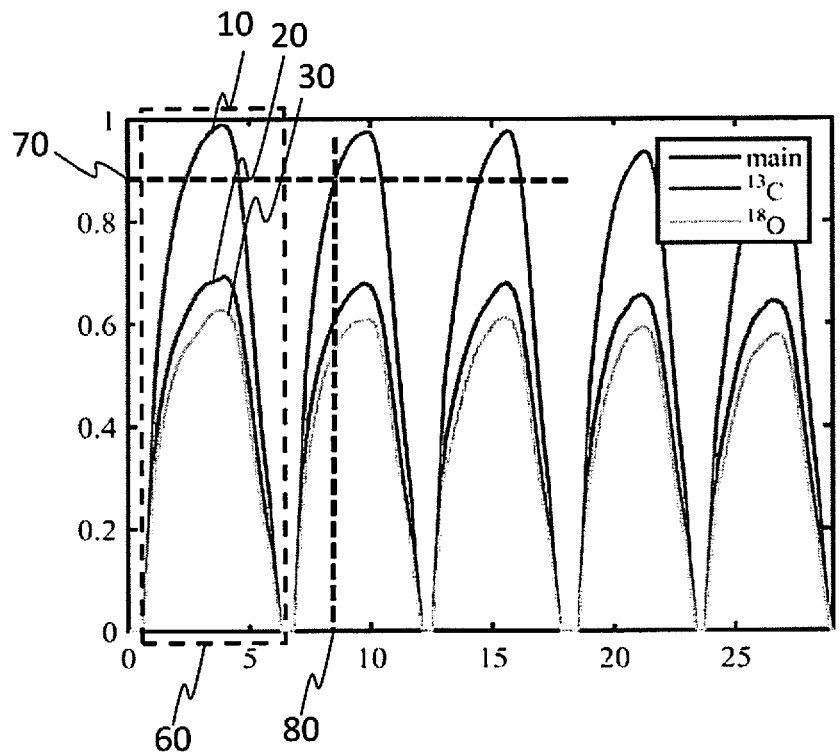
FIG. 3 shows a principle of breath analysis according to a method according to an embodiment of the invention.

FIG. 3 shows a principle of breath analysis according to a method according to an embodiment of the invention. The graph shows a measured absorption of light in the analyzer at the vertical axis and time in seconds at the horizontal axis as in FIG. 1. FIG. 3 shows a first respiratory cycle 60 of a person, for example a patient, during which the absorption is measured with an apparatus according to the embodiment of the invention. From the first determined cycle a threshold 70 is determined. The threshold is in an embodiment a predetermined measured the absorption of a selected isotopologue or a concentration of a measured species, such as $CO_2$. Based on the threshold 70, a sampling or a measurement time 80, i.e. a time or a time frame at which the measurement of isotope ratios or a concentration of a measured species, such as $CO_2$ is carried out, is determined for the second, i.e. following, breath cycle. The sampling 80 time is determined based on the threshold 70, i.e. the start of the measurement is triggered at the threshold. In an embodiment, the objective is to choose the threshold 70 and accordingly the sampling time in such a way that it is at a point well along the breath cycle at appoint in which the isotope ratios differ significantly, but not too far along the breath cycle when the difference starts to diminish as seen from FIG. 2. The sampling time 80 is shown as a single point of time in FIG. 2, but it is to be noted that the sampling time or the measurement time 80 refers to the point of time or a time frame during which the sampling of the case and the measurement from the sampled gas is carried out. The point of time, or the start of the time frame, is triggered by reaching the threshold.

The chosen sampling time 80, the start of which is triggered by the threshold 70, ascertains that the isotope ratios, or a concentration of a measured species, such as $CO_2$, in breath, measured are representative of the exhaled breath not only from the upper parts of the respiratory system and that the isotope ratios have as large a difference as possible in order to achieve an improved sensitivity of measurement. As the sampling time 80 is chosen based on the actual determined first breath cycle, the uncertainty related to sampling at a random time or gathering a sample during the whole or part of the breath cycle is removed. Furthermore, as the threshold 70 and the sampling time 80 is determined based on the first breath cycle, possible errors due to person-to-person variability of the isotope ratios is removed.

Figure 4:
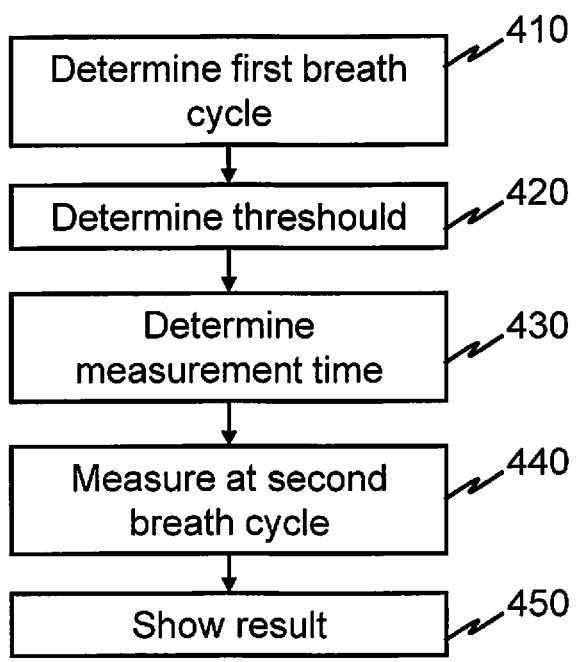
FIG. 4 shows a flow chart of a method according to an embodiment of the invention.

FIG. 4 shows a flow chart of a method according to an embodiment of the invention. The person whose breath is being measured breathes in to an apparatus according to the invention. The breathing is carried out normally, i.e. the person need not breathe in any particular predetermined manner. At 410 a first breath cycle 60 is determined, i.e. the absorptions caused by the different isotopologues are measured during the first breath cycle. The breath cycle herein refers to a single exhalation of the person, the isotopic composition profile, or concentration profile of a measured species, such as $CO_2$, of which is measured. It is to be noted the first breath cycle need not be the first breath cycle that is breathed in to the apparatus, but the first cycle after commencing the determination method.

At 420 a threshold 70 is determined based on the first breath cycle that was measured as hereinbefore described with reference to FIG. 3. At 430 a sampling time 80, or a time frame, is determined based on the threshold 70. At 440 the measurement of isotopic composition, or a concentration of a measured species, such as $CO_2$, in breath, is carried out at or during the previously determined sampling time 80 for a second breath cycle. It is to be noted the second breath cycle need not be the second breath cycle, i.e. the breath cycle immediately following the first breath cycle, but can be any breath cycle after the first breath cycle. Ideally, the breath cycles are substantially identical, i.e. the person breathing into the apparatus breathes substantially steadily.

At 450 the result of the determination of the isotopic composition, or a concentration of a measured species, such as $CO_2$, in breath, is shown. In an embodiment, the isotopic composition, or concentration, is shown as value of a ratio of the determined isotopologues, i.e. as a 12C/13C and/or 18O/16O ratio. In a further example embodiment, it is shown whether the ratio, or concentration, is below or above a certain predetermined value, for example a value representing a threshold value indicative of a certain condition that can be diagnosed from the ratio or concentration. In a further embodiment, the result of the measurement is compared to a previously, for example a certain predetermined time, dependent on the purpose, before the current measurement, measured value.

Figure 5:
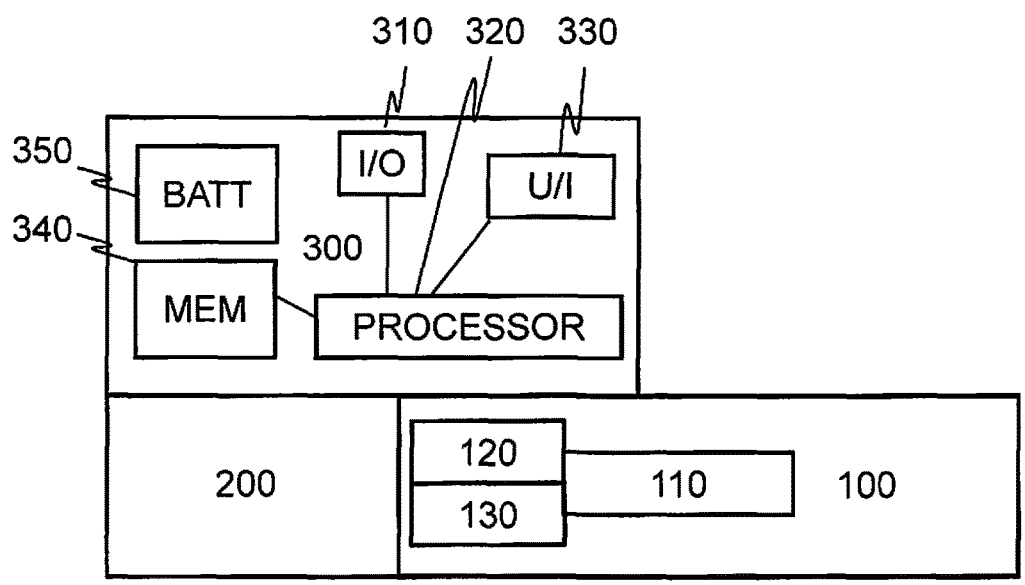
FIG. 5 shows a schematic block view of an apparatus according to an embodiment of the invention.

FIG. 5 shows a schematic block view of an apparatus according to an embodiment of the invention. The apparatus comprises a measurement unit 100 comprising, in an embodiment, a multipass cell 110 configured to provide a volume in which the breath sample is held or conducted through for measurement. The apparatus further comprises an optical unit 120 comprising an optical source, in an embodiment a laser source, configured to send light, in an embodiment laser light, through the multipass cell 110. The optical unit further comprises a detector configured to receive the light having traversed the multipass cell and the sample of exhaled gas contained therein. In an embodiment, the measurement unit 100 further comprises a gas handling unit 130 configured to conduct the gas, i.e. the exhaled air to the multipass cell 110, in an embodiment to hold the gas in the multipass cell 110 for a certain time and configured to enable the sample to flow away from the multipass cell 110.

The apparatus further comprises a sampling unit 200 configured to enable the gas, in an embodiment the exhaled air to be conducted to the measurement unit. In an embodiment, the sampling unit comprises a nozzle or inlet in which the person breathes or in which the gas is conducted from or through a further source. In a further embodiment, the sampling unit is a part of a further apparatus, such as a breathing test apparatus used for medical purposes or for study of athletes.

The apparatus further comprises a control unit 300. In an embodiment, the control unit 300 comprises, or is comprised in, a separate device or comprises a separate element integrated with the apparatus. The control unit 300 comprises electronics configured to control the operations of the apparatus, to carry out calculations and to cause carrying out the steps of the method according to the invention. In an embodiment, if separate, the control unit 300 is connected to the apparatus in a conventional manner, for example with wires or wirelessly with e.g. wireless local area network or near field communication such as Bluetooth or Near Field Communication, NFC, in which case the required communication components are provided on the measurement unit 100 and the control unit 300.

The control unit 300 comprises a memory 340 and a processor 320. The processor 320 is configured to retrieve data from the detector element in the optical unit 120 of the measurement unit and to cause storing the data into the memory 340. The processor 320 is further configured to cause controlling of the operation of the measurement unit 100, the sampling unit 200 and the control unit 300 itself using a non-transitory computer program code stored in the memory 340.

In a further embodiment, the control unit 300 comprises a communication unit 310 comprising, for example, a local area network (LAN) port; a wireless local area network (WLAN) unit; Bluetooth unit; cellular data communication unit; near field communication unit or satellite data communication unit. The control unit further comprises a power source, such as a battery 350 or a connection to external power.

In a further embodiment the control unit 300 comprises a user interface unit 330 comprising for example a display or a touch display for showing the measurement result. In further embodiment the user interface unit 330 comprises a simplified display, such as led array or lights of different colors, for example light emitting diodes, for indicating the result of the measurement. In a still further embodiment, the apparatus 100 is a diagnostic apparatus and is configured to indicate, e.g. show on a display, whether the determined isotopic composition is indicative of a condition or a disease.

In a still further embodiment, the control element 300 comprises, or is comprised in, a personal electronic device such as a wristwatch, a smart watch, an activity bracelet, a mobile phone, a smartphone, a tablet, a computer or a television, configured to co-operate with the measurement unit 100.

Some use cases relating to given embodiments of determining the isotopic composition of breath, or a concentration of a measured species, such as $CO_2$, in breath, are presented in the following. In a first use case, the apparatus according to an embodiment is used as a diagnostic apparatus in order to diagnose a condition or disease of a human or an animal. Examples of such conditions and diseases include but are not limited to sepsis using 13C/12C and or 18O/16O isotope ratio, helicobacter pylori using 13C/12C and or 18O/16O isotope ratio and type 2 diabetes using 18O/16O isotope ratio.

In a second use case, the apparatus and method according to an embodiment is used to determine isotopic composition of breath in order to monitor energy usage of an athlete, for example during training and/or competition.

In a third use case, the apparatus and method according to an embodiment is used to determine isotopic composition of breath in order to monitor energy usage as an individual weight loss aid.

It is to be noted that although the embodiments of the invention have been described with reference to determining the isotopic composition of breath, i.e. exhaled air, the hereinbefore described embodiments of the invention are applicable in an analogous manner to further gas analysis, in which the gas to be measured has a cycle during which the isotopic ratios, or further ratios of interest, change in such a way that the sampling time affects the result and/or sensitivity of the measurement.

Without in any way limiting the scope, interpretation, or application of the claims appearing below, a technical effect of one or more of the example embodiments disclosed herein is an increased sensitivity and reliability of determination of isotopic composition, or a concentration of a measured species, such as $CO_2$, in breath. Another technical effect of one or more of the example embodiments disclosed herein is a possibility of real-time isotopic composition analysis. Another technical effect of one or more of the example embodiments disclosed herein is the provision of a reliable and compact apparatus for determination of isotopic composition.

Although various aspects of the invention are set out in the independent claims, other aspects of the invention comprise other combinations of features from the described embodiments and/or the dependent claims with the features of the independent claims, and not solely the combinations explicitly set out in the claims.

It is also noted herein that while the foregoing describes example embodiments of the invention, these descriptions should not be viewed in a limiting sense. Rather, there are several variations and modifications which may be made without departing from the scope of the present invention as defined in the appended claims.

The invention claimed is:
1. A method for breath analysis, comprising:
 determining an isotopic composition profile of a first breath cycle;

determining a threshold by determining a predetermined absorption of a selected isotopologue, wherein the threshold is selected based on a difference between a first isotope ratio and a second isotope ratio;

determining a sampling time; and measuring the isotopic composition, during a second breath cycle at the sampling time triggered by reaching the threshold.

2. The method of claim 1, further comprising showing as a result the measured isotopic composition.

3. The method of claim 1, wherein determining an isotopic composition profile of a first breath cycle comprises measuring an absorption of various isotopologues of carbon dioxide.

4. The method of claim 1, wherein determining a sampling time comprises determining a time or a time frame on or during which the measurement is carried out during the second breath cycle.

5. The method of claim 1, wherein the threshold is selected at a point along the first breath cycle in which the difference between the first isotope ratio and the second isotope is the greatest.

6. A non-transitory memory medium comprising a computer program comprising computer code for causing performing the method of claim 1, when executed by an apparatus.

7. An apparatus for breath analysis, comprising
a measurement unit configured to measure an absorption of various isotopologues of carbon dioxide during a breath cycle;
a sampling unit configured to enable exhaled breath to be conducted to the measurement unit; and
a control unit configured to cause the apparatus to:
determine an isotopic composition of a first breath cycle;
determine a threshold by determining a predetermined absorption of a selected isotopologue, wherein the threshold is selected based on a difference between a first isotope ratio and a second isotope ratio;
determine a sampling time based on the threshold; and
measure the isotopic composition during a second breath cycle at the sampling time triggered by reaching the threshold.

8. The apparatus of claim 7, wherein the measurement unit comprises:
a multipass cell;
an optical unit comprising an optical source and a detector; and
a gas handling unit.

9. The apparatus of claim 7, wherein the sampling unit comprises an inlet into which the breath to be measured is conducted to.

10. The apparatus of claim 7, wherein the control unit comprises a processor configured to control the apparatus.

11. The apparatus of claim 7, wherein the control unit comprises a user interface unit configured to show a result of the determination of isotopic composition.

12. The apparatus of claim 7, wherein the apparatus is configured to show whether a result of the determination of the isotopic composition of breath is indicative of a disease or a condition.

13. The apparatus of claim 7, wherein the threshold is selected at a point along the first breath cycle in which the difference between the first isotope ratio and the second isotope is the greatest.

* * * * *